United States Patent [19]

Fedin et al.

[11] Patent Number: 5,010,106

[45] Date of Patent: Apr. 23, 1991

[54] METHOD OF STERILIZING ANTHERS OF PLANTS

[76] Inventors: Marat A. Fedin, ulitsa Dm. Ulyanova, 24, kv. I58; Tatyana A. Kuznetsova, Khoroshevskoe shosse, 36b, kv. 62, both of Moscow; Viktor I. Lysenkov, ulitsa Yakubova, 30, kv. 366, Minsk; Svetlana A. Novikova, ulitsa Shirokaya, I9, korpus 2, kv. I76, Moscow; Valentin A. Savchuk, opytnaya stantsia VIR, Poltavskaya oblast, Globinsky raion, selo Ustimovka; Anatoly I. Sedelnikov, ulitsa Turgeneva, 24b, kv. 54, Gorky; Vera P. Shabunya, ulitsa M. Gorkogo, 50, kv. 24; Boris G. Udarov, ulitsa Yakuba Kolasa, 72, kv. 39, both of Minsk; Tatyana S. Tikhonova, ulitsa Aktjubinskaya, 3, kv. 5; Nina P. Polyakova, ploschad Svobody, 4, kv. 85, both of Gorky; Sergei I. Paklin, ulitsa Malaya Filevskaya, 66, kv. 30, Moscow, all of U.S.S.R.

[21] Appl. No.: 439,030

[22] PCT Filed: Mar. 17, 1988

[86] PCT No.: PCT/SU88/00062

§ 371 Date: Nov. 1, 1989

§ 102(e) Date: Nov. 1, 1989

[87] PCT Pub. No.: WO89/08394

PCT Pub. Date: Sep. 21, 1989

[51] Int. Cl.$^5$ .................. A01N 27/00; A01N 31/00
[52] U.S. Cl. ................. 514/546; 514/729; 514/763
[58] Field of Search ............ 514/763, 729, 546

Primary Examiner—Stanley J. Friedman
Assistant Examiner—Russell Travers
Attorney, Agent, or Firm—Burgess, Ryan & Wayne

[57] ABSTRACT

A method is provided for sterilizing anthers of plants, such as Gramineae or *Helianthus annuus* (sunflower) by applying a sterilizing agent to the plants at the fifth and/or sixth stage of organogenesis, chosen from among terpenoid compounds of the methylcyclohexene series.

11 Claims, No Drawings

METHOD OF STERILIZING ANTHERS OF PLANTS

BACKGROUND OF THE INVENTION

1. Field of the Art

The present invention relates to the art of biology and agriculture and, more particularly, to a method of sterilizing anthers of plants which is used in selection and seed production.

2. Description of the Prior Art

At the present time the world is facing the problem of intensification of agriculture, in particular of raising yields of grain crops, fodder, vegetable and industrial plants by way of an extensive application of the first-generation hybrids. Due to the heterosis phenomenon these hybrids are distinguished from the parental forms by a higher (by 25-30%) productivity and a better quality of the products. Known is a method for breeding novel hybrids which is based on a "cytoplasmic male sterility-fertility reductants" system. This method is based on a long-term (12-14 years) and complicated selection work involving the creation of sterile analogs, sterility-fixing agents and fertility reductants. Most promising are methods based on sterilization of anthers of plants by chemical sterilizing agents (gametocides). The use of gametocides proves to be much more economically efficient than the use of the "cytoplasmic male sterility" system, since there is no necessity in creating such forms as a sterile analog, an analog of sterility fixation in maternal forms and an analog of fertility reduction in paternal ones. In fact it is possible to obtain seeds of the first-generation hybrids both in the course of the selection studying of the initial forms and in the organization of their industrial production.

By now about 200 compounds have been found which display a gametocidal activity and belong to different classes of chemical compounds as regards their chemical structure. Gametocides must cause maximum full male sterility in the treated plants, while preserving the viability of ovicells and ensuring settability in free pollination at a sufficiently high level (preferably not less than 70% of the control). Their phytotoxicity and toxicity for the warm-blooded must be minimal.

Known in the art are methods of sterilizing the anthers of gramineous crops (L. J. Nickell. Plant Growth Regulators. Applications in Agriculture. Moscow, "Kolos" Publishers, 1984, pp. 28-31; SU, A, No. 906457) which comprise treating the plants with sterilizing agents such as 2-chloroethylphosphonic acid (Ethrel), maleic acid hydrazide, di-(polyfluoroalkyl)-phosphoric acids and salts thereof and the like. The treatment of the plants with the sterilizing agents is effected at the V-th or VI-th stage of organogenesis (after F. M. Kuperman).

At the V-th stage of organogenesis the processes of the formation and differentiation of florets begin. At the end of this stage neoplasms originate: sporogeneous archisporeal tissues. At this stage the initiation of stamina, pistil and integumentary organs of the floret occurs. At the V-th stage the beginning of differentiation of the stamen primordium into a connective and pistil is observed. The VI-th stage is characterized by the processes of the floret formation (micro- and macro-sporogenesis). At this stage individual mononuclear pollen grains are usually formed (F. M. Kuperman, "Morphophysiology of Plants", Moscow, "Vysshaya Shkola" Publishers, 1973, pp. 30-36).

Also known in the art is a method of sterilizing the anthers of gramineous plants (GB, A, No. 1567153), which comprises treating the gramineous plants with a sterilizing agent during the period between the appearance of the second internode and earing. As the sterilizing agent use is made of heterocyclic compounds, the main representatives thereof being 2-carboxy-3,4-methanopyrrolidine or 2-methoxycarbonyl-3,4-methanopyrrolidine. These compounds are used in combination with diluents and surfactants.

SUMMARY OF THE INVENTION

The present invention is directed to the selection of novel sterilizing agents and to a method enabling its application for sterilization of anthers of a wide range of crops with a high efficiency of sterilization, while preserving a high settability of seeds in open pollination.

This object is accomplished by provides a method of sterilizing anthers of plants by way of treatment thereof with a sterilizing agent in combination with a diluent during the period of the fifth and/or sixth stage of Organogenesis. In accordance with the present invention, as the sterilizing agent use is made of terpenoid compounds of the general formula:

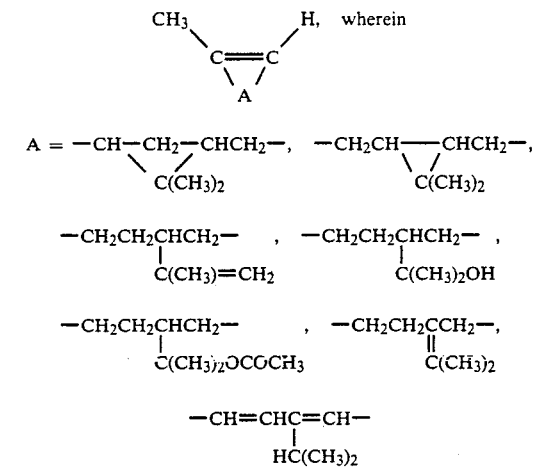

or mixtures thereof. The sterilizing agent can be used in combination with any known acceptable diluent. It is advisable to use it in combination with water in the form of a 0.1-2% aqueous emulsion. As the plants to be treated with the above-specified sterilizing agent, it is preferable to use gramineous plants or sunflower.

The method according to the present invention makes it possible to attain male sterility of the plants (98-100%) and to retain a high percentage of settability of seeds (above 70%). In order to ensure a high level of sterilization of anthers under non-favourable climatic conditions, a repeated treatment of the plants with the sterilizing agent is carried out during the periods of the fifth and/or sixth stage of organogenesis (after Kuperman).

PREFERRED EMBODIMENT OF THE INVENTION

The method according to the present invention is carried out in the following manner.

Plants such as winter and spring wheat, diploid and tetraploid rye, triticale, millet, sunflower are treated with a sterilizing agent; as such an agent use is made of terpenoid compounds of the general formula:

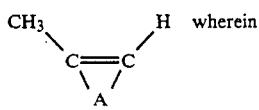

wherein

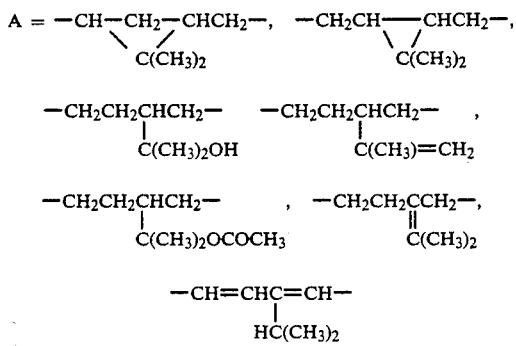

or mixtures thereof. The terpenoid compounds can be used in combination with any acceptable diluents. It is advisable to use water as the diluent. It is preferable to use a 0.1-2% aqueous emulsion of the above-mentioned compounds.

When desired, any suitable surfactants can be added to the working solutions. Usually it is advisable to add any known auxiliary additives such as wetting agents, dispersing agents, adhesives to the working solutions while applying them to the plants.

The sterilizing agent can be applied to the plants by various treatment methods such as hydraulic spraying, or air spraying (aerosols). The treatment of the plants with the sterilizing agent is carried out during the period of the fifth and/or sixth stage of organogenesis (after Kuperman). The dose of the sterilizing agent depends on the nature of the compound, the crop being treated, the stage of the treatment and on the natural climatic factors. In order to ensure a high sterilizing effect under unfavourable climatic conditions, it is advisable that repeated treatment of the plants be carried out at the VI-th stage of organogenesis. The total dose of the sterilizing agent is varied within the range of 0.6 to 20 kg/ha.

All the terpenoid compounds according to the present invention, which are employed as the sterilizing agent have been tested for toxicity in experiments on animals. The results of the experiments have shown that these compounds are low-toxic or substantially non-toxic.

Thus, the $LD_{50}$ of α-terpeniol is 4,300 mg/kg, while the $LD_{50}$ of α-pinene is 3,700 mg/kg.

All the terpenoid compounds according to the present invention are naturally-occurring compounds which are obtained from the gum of coniferous plants.

The presence of the gametocidal activity in the sterilizing agents according to the present invention has been revealed in field tests in different soil and climatic zones on 10 m² plots in 2-3 and 4-fold tiers. Each sterilizing agent has been tested for at least 5 years.

The occurrence of the organogenesis stages is controlled cytologically. The treatment of the plants with the sterilizing agent is carried out at the beginning of the fifth stage of organogenesis according to Kuperman.

In the course of earing, the main ears and other tiers are isolated by means of parchment isolators. For wheat and triticale individual isolators are used. For rye 1 ear from 5 to 7 different adjacent plants is brought under one common isolator. For millet each panicle is isolated individually. The percentage of sterility (X) for wheat, rye, triticale and millet is calculated according to the formula:

$$X = \left[ 1 - \frac{\text{the number of seeds set under the isolator in the treated plants}}{\text{the number of seeds set under the isolator in the untreated control plants}} \times 100\% \right]$$

The number of seeds in the non-isolated ears of the control plants is assumed to be a 100% settability in open pollination.

To obtain reliable data, 20-25 isolators are used from each tier for wheat and triticale, 10-15 isolators from each tier are used for rye and millet.

To control the chemical sterilization of sunflower pollen, 45 treated plants on each tier are used for each compound, of which 15 plants are isolated for self-pollination, the heads of 15 other plants are pollinated with a mixture of pollen gathered on 20-25 treated isolated heads, and 15 plants are left for open pollination to check the settability of the achenes with the paternal-form pollen.

The male sterility of sunflower plants is evaluated by the results of fertility and viability of pollen, morphological features of spermatozoa and settability of achenes when pollinating the treated isolated plants with pollen of the non-treated parental form. The viability of the ovicell is determined from the setting of seeds in the treated plants in open pollination with the paternal-form pollen.

The treatment of plants should be preferably carried out in clear calm weather. All the compounds penetrate into the plant tissues within the period of 4 hours. In the case of rainfall during the 4-hours' period a repeated treatment of the plants at the VI-th stage of organogenesis is necessary.

For a better understanding of the present invention, some specific examples illustrating the embodiments of the method according to the invention are given hereinbelow.

EXAMPLES 1 TO 6

Plants of winter wheat of Mironovskaya 808 variety are treated at the V-th stage of organogenesis (after Kuperman) by way of spraying, from a knap-sack sprayer, with a 2% aqueous emulsion of the following sterilizing agents: 1-n-mentene-8-ol, 1-n-mentenyl-8-acetate, 3-carene, 1,-4-(8)-n-mentadiene, 1,8-n-mentadiene, n-cymene respectively. As the emulsifying agent use is made of 0.1% by mass of a calcium $C_{12}$-$C_{14}$-alkylbenzene sulphonate. As the adjuvant introduced into the emulsion is 0.01% by mass of dodecylsulphate. The rate of consumption of the preparation is 12 kg/ha. Serving as the control are the plants treated with the diluent without the sterilizing agent. The results of the tests are shown in Table 1 hereinbelow. Similar results are obtained in the treatment of the plants at the VI-th stage of organogenesis.

EXAMPLES 7 TO 13

Plants of spring wheat of Moskovskaya 35 variety are treated at the VI-th stage of organogenesis with a 1% aqueous emulsion of the following sterilizing agents:

TABLE 1

| No. | Example No. | Number of grains in ear under isolator | Sterility percentage, % | Number of grains in ear in open pollination | Percentage of setting of seeds in open pollination, % |
|---|---|---|---|---|---|
| 1 | Control | 40.6 | 0.0 | 42.6 | 100.0 |
| 2 | Example 1 | 0.0 | 100.0 | 40.1 | 94.1 |
| 3 | Example 2 | 0.0 | 100.0 | 38.8 | 91.1 |
| 4 | Example 3 | 0.0 | 100.0 | 39.7 | 93.2 |
| 5 | Example 4 | 0.6 | 98.5 | 40.2 | 94.4 |
| 6 | Example 5 | 3.8 | 90.7 | 41.8 | 98.1 |
| 7 | Example 6 | 0.7 | 98.3 | 39.9 | 93.7 |

α-terpeniol, 1-n-mentenyl-8-acetate, 3-carene, 1,-4-(8)-n-mentadiene, 1,8-n-mentadiene, n-cymene, α-pinene respectively. The emulsion contains, as the emulsifying agent, 0.1% by mass of a calcium $C_{12}$–$C_{14}$-alkylbenzene sulphonate and as the adjuvant −0.01% by mass of N,N-dimethylformamide. The rate of consumption of the preparation is 8 kg/ha. Serving as the control are the plants treated with the diluent without the sterilizing agent. The results of the tests are shown in Table 2 hereinbelow. Similar results have been obtained in the treatment of the plants at the V-th stage of organogenesis.

EXAMPLES 14–20

Plants of spring wheat of Botanicheskaya 4 variety are treated at the V-th stage of organogenesis with a 1% aqueous emulsion of the following sterilizing agents: 3-carene, n-cymene, α-pinene, α-terpeniol, 1,-4-(8)-n-menyadiene, 1,8-n-mentadiene, 1-n-mentenyl-8-acetate respectively. The emulsion contains, as the emulsifying agent, 0.1% by mass of a calcium $C_{12}$–$C_{14}$-alkyl-benzene sulphonate and, as the adjuvant −0.01% by mass of tetrahydrofuran. The rate of consumption of the preparation is 6 kg/ha. Serving as the control are the plants treated in a manner similar to that described in Example 1 hereinbefore. The results of the tests are shown in Table 3. Similar results are obtained in the treatment of the plants in the VI-th stage of organogenesis.

TABLE 2

| No. | Example No. | Number of grains in ear under isolator | Sterility percentage, % | Number of grains in ear in open pollination | Percentage of grain setting in open pollination, % |
|---|---|---|---|---|---|
| 1. | Control | 29.4 | 0.0 | 31.2 | 100.0 |
| 2. | Example 7 | 0.0 | 100.0 | 27.2 | 87.2 |
| 3. | Example 8 | 0.0 | 100.0 | 28.6 | 91.7 |
| 4. | Example 9 | 0.2 | 99.3 | 29.0 | 92.9 |
| 5. | Example 10 | 0.0 | 100.0 | 28.1 | 90.1 |
| 6. | Example 11 | 0.8 | 97.3 | 30.0 | 96.2 |
| 7. | Example 12 | 1.2 | 95.9 | 27.3 | 87.5 |
| 8. | Example 13 | 0.0 | 100.0 | 28.7 | 91.0 |

TABLE 3

| No. | Example No. | Number of grains in ear under isolator | Percentage of sterility, % | Number of grains in ear in open pollination | Percentage of grain setting in open pollination, % |
|---|---|---|---|---|---|
| 1. | Control | 28.9 | 0.0 | 30.9 | 100.0 |
| 2. | Example 14 | 0.0 | 100.0 | 27.8 | 90.0 |
| 3. | Example 15 | 1.2 | 95.9 | 30.1 | 97.4 |
| 4. | Example 16 | 0.0 | 100.0 | 29.2 | 94.5 |
| 5. | Example 17 | 0.0 | 100.0 | 28.4 | 91.9 |
| 6. | Example 18 | 0.0 | 100.0 | 29.5 | 95.5 |
| 7. | Example 19 | 0.8 | 97.2 | 27.3 | 88.3 |
| 8. | Example 20 | 0.0 | 100.0 | 29.5 | 95.5 |

EXAMPLES 21 to 23

Plants of diploid rye of Chulpan variety are treated at the VI-th stage of organogenesis (after Kuperman) by way of spraying, from a knap-sack sprayer, a 1.0% aqueous emulsion of 1,4-(8)-n-mentadiene, 1,8-n-mentadiene or p-cymene respectively. The emulsion contains 0.1% by mass of calcium $C_{12}$–$C_{14}$-alkylbenzene sulphonate and 0.01% by mass of dodecylsulphate. The rate of consumption of the sterilizing agent is 10 kg/ha. Serving as the control are the plants treated in a manner similar to that described in Example 1. The results of the tests are shown in Table 4 hereinbelow. Similar results are obtained in the treatment of the plants at the V-th stage of organogenesis.

TABLE 4

| No. | Example No. | Number of grains in ear under isolator | Sterility percentage, % | Number of grains in ear in open pollination | Percentage of grain setting in open pollination, % |
|---|---|---|---|---|---|
| 1. | Control | 44.1 | 0.0 | 49.6 | 100.0 |
| 2. | Example 21 | 0.8 | 97.8 | 47.8 | 96.4 |
| 3. | Example 22 | 0.3 | 99.2 | 43.2 | 87.1 |
| 4. | Example 23 | 0.0 | 100.0 | 47.4 | 95.6 |

EXAMPLES 24–27

Plants of tetraploid rye of Ukrainskaya tetra variety are treated in a manner similar to that described in Example 1 hereinbefore. In so doing, use is made of a 1% aqueous emulsion of the following sterilizing agents: 2-pinene, α-terpeniol, terpenylacetate, 3-carene. The rate of consumption of the sterilizing agent is 8 kg/ha. Serving as the control are the plants treated with the diluent without the sterilizing agent. The results of the tests are shown in Table 5 hereinbelow.

TABLE 5

| No. | Example No. | Number of grains in ear under isolator | Sterility percentage, % | Number of grains in ear in open pollination | Percentage of grain setting in open pollination, % |
|---|---|---|---|---|---|
| 1. | Control | 28.0 | 0.0 | 36.8 | 100.0 |
| 2. | Example 24 | 0.0 | 100.0 | 36.3 | 98.6 |
| 3. | Example 25 | 0.4 | 98.6 | 33.8 | 91.8 |
| 4. | Control | 36.1 | 0.0 | 40.2 | 100.0 |
| 5. | Example 26 | 0.0 | 100.0 | 32.8 | 81.6 |
| 6. | Example 27 | 0.1 | 99.6 | 37.3 | 92.8 |

EXAMPLES 28–29

Plants of diploid rye of Kharkovskaya 55 variety are treated, in a manner similar to that of Example 1, with a 1% aqueous emulsion of the following sterilizing agents: terpenylacetate and 3-carene respectively. The rate of consumption of the sterilizing agent is 6 kg/ha. The results of the tests are shown in Table 6 hereinbelow.

TABLE 6

| No. | Example No. | Number of grains in ear under isolator | Sterility percentage, % | Number of grains in ear in open pollination | Percentage of grain setting in open pollination, % |
|---|---|---|---|---|---|
| 1. | Control | 31.5 | 0.0 | 39.4 | 100.0 |
| 2. | Example 28 | 0.1 | 99.7 | 35.2 | 89.3 |
| 3. | Example 29 | 0.6 | 98.1 | 36.7 | 93.1 |

EXAMPLES 30–31

Plants of triticale of PRAG-109 variety are treated at the V-th stage of organogenesis, in a manner similar to that of Example 1 hereinbefore, with a 2% aqueous emulsion of the following sterilizing agents: terpenylacetate and 3-carene respectively. The rate of consumption of the sterilizing agent is 12 kg/ha. The results of the tests are shown in Table 7 hereinbelow. Similar results are obtained in the treatment of the plants at the VI-th stage of organogenesis.

TABLE 7

| No. | Example No. | Number of grains in ear under isolator | Sterility percentage, % | Number of grains in ear in open pollination | Percentage of grain setting in open pollination, % |
|---|---|---|---|---|---|
| 1. | Control | 41.3 | 0.0 | 45.8 | 100.0 |
| 2. | Example 30 | 0.0 | 100.0 | 40.9 | 89.3 |
| 3. | Example 31 | 0.3 | 99.3 | 37.6 | 82.1 |

EXAMPLES 32–33

Plants of triticale of Amphidiploid 206 variety are treated at the VI-th stage of organogenesis, in a manner similar to that described in Example 1, with a 2% aqueous emulsion of the following sterilizing agents: terpenylacetate and 3-carene respectively. The rate of consumption of the sterilizing agent is 12 kg/ha. The results of the tests in comparison with the control are shown in Table 8 hereinbelow. Similar results are obtained in the treatment of the plants at the V-th stage of organogenesis.

TABLE 8

| No. | Example No. | Number of grains in ear under isolator | Sterility percentage, % | Number of grains in ear in open pollination | Percentage of grain setting in open pollination, % |
|---|---|---|---|---|---|
| 1. | Control | 23.4 | 0.0 | 25.2 | 100.0 |
| 2. | Example 32 | 0.4 | 97.8 | 23.0 | 91.3 |
| 3. | Example 33 | 0.0 | 100.0 | 23.8 | 94.4 |

EXAMPLES 34–39

Plants of millet of Mironovskoye 94 variety are treated at the V-th stage of organogenesis, in a manner similar to that of Example 1, with a 1% aqueous emulsion of the following sterilizing agents: terpenylacetate, 3-carene, 1,4-(8)-n-mentadiene, 1,8-n-mentadiene, n-cymene, α-terpeniol respectively. The rate of consumption of the sterilizing agent is 10 kg/ha. The results of the tests in comparison with the control are shown in Table 9. Similar results are obtained in the treatment of the plants at the VI-th stage of organogenesis.

EXAMPLE 40

Plants of spring wheat of Botanicheskaya 4 variety are treated as described in Example 1 hereinbefore at the VI-th stage of organogenesis with a 1% aqueous emulsion of a sterilizing agent mixture, namely: 1,4-(8)-n-mentadiene and n-cymene employed in the ratio of 1:1. The rate of consumption of the mixture of the sterilizing agents is 6 kg/ha. The results of the tests are shown in the following Table 10. Similar results are obtained in the treatment of the plants at the V-th stage of organogenesis.

TABLE 9

| No. | Example No. | Number of grains in panicle under isolator | Sterility percentage, % | Number of grains in panicle in open pollination | Percentage of grain setting in open pollination, % |
|---|---|---|---|---|---|
| 1. | Control | 124.9 | 0.0 | 145.4 | 100.0 |
| 2. | Example 34 | 0.0 | 100.0 | 138.9 | 95.5 |
| 3. | Example 35 | 0.0 | 100.0 | 89.1 | 62.3 |
| 4. | Example 36 | 0.0 | 100.0 | 137.3 | 89.6 |
| 5. | Example 37 | 0.0 | 100.0 | 109.3 | 71.1 |
| 6. | Example 38 | 0.0 | 100.0 | 107.3 | 70.0 |
| 7. | Example 39 | 0.0 | 100.0 | 128.5 | 86.0 |

EXAMPLE 41

Plants of spring wheat of Rodina variety are treated in a manner similar to that of Example 1 at the VI-th stage of organogenesis with a 1% aqueous emulsion of a mixture of the sterilizing agents, viz. 3-carene and α-terpeniol employed in the ratio of 1:1. The rate of consumption of the mixture of the sterilizing agents is 6 kg/ha. The results of the tests are shown in Table 11 hereinbelow. Similar results are obtained in the treatment of the plants at the V-th stage of organogenesis.

TABLE 10

| No. | Treatment of the plants | Number of grains in ear under isolator | Sterility percentage, % | Number of grains in ear in open pollination | Percentage of grain setting in open pollination, % |
|---|---|---|---|---|---|
| 1. | Control | 28.9 | 0.0 | 30.9 | 100.0 |
| 2. | With the mixture of the sterilizing | 0.0 | 100.0 | 27.4 | 88.7 |

TABLE 13

| No. | Example No. | Percentage of setting of achenes pollination with the pollen mixture under isolator | Percentage of setting in open pollination, % | Mass of 1,000 achenes, g | Number of sterile plants, % | Oil content of achenes, % | Germination rate of achenes, % |
|---|---|---|---|---|---|---|---|
| | | Sunflower of Peredovik variety | | | | | |
| 1. | Control | 85.0 | 85.0 | 84.0 | 0.0 | 54.7 | 100.0 |
| 2. | Example 45 | 0.0 | 80.0 | 82.3 | 100.0 | 53.4 | 100.0 |
| 3. | Example 46 | 0.0 | 85.3 | 84.0 | 100.0 | 53.6 | 100.0 |
| | | Sunflower of BK-119 line | | | | | |
| 4. | Control | 72.6 | 85.0 | 60.0 | 0.0 | 51.0 | 100.0 |
| 5. | Example 47 | 0.0 | 80.4 | 55.4 | 100.0 | 49.4 | 100.0 |
| 6. | Example 48 | 0.0 | 82.5 | 56.7 | 100.0 | 51.7 | 100.0 |

TABLE 11

| No. | Treatment of the plants | Number of grains in ear under isolator | Sterility percentage, % | Number of grains in ear in open pollination | Percentage of grain setting in open pollination, % |
|---|---|---|---|---|---|
| 1. | Control | 29.5 | 0.0 | 35.0 | 100.0 |
| 2. | With the mixture of the sterilizing agents | 0.0 | 100.0 | 29.4 | 84.0 |

EXAMPLES 42–44

Plants of diploid rye of Chulpan variety are treated in a manner similar to that of Example 1 at the VI-th stage of organogenesis with a 1% aqueous emulsion of the following mixtures of the sterilizing agents: 2-pinene with 1.8-n-mentadiene (in the ratio of 1:1), terpenylacetate with n-cymene (in the ratio of 1:1), 3-carene with terpenylacetate (in the ratio of 1:1). The rate of consumption of the sterilizing agents is 6 kg/ha. The results of the tests are shown in Table 12 hereinbelow. Similar results are obtained in the treatment of the plants at the V-th stage of organogenesis.

TABLE 12

| No. | Example No. | Number of grains in ear under isolator | Sterility percentage, % | Number of grains in ear in open pollination | Percentage of grain setting in open pollination, % |
|---|---|---|---|---|---|
| 1. | Control | 44.5 | 0.0 | 46.6 | 100.0 |
| 2. | Example 42 | 0.0 | 100.0 | 43.3 | 92.9 |
| 3. | Example 43 | 0.0 | 100.0 | 38.0 | 81.5 |
| 4. | Example 44 | 0.0 | 100.0 | 46.2 | 99.2 |

EXAMPLES 45 TO 48

Plants of sunflower of Peredovik variety and of BK-119 line are treated in a manner similar to that described in Example 1 hereinbefore at the V-th stage of organogenesis with a 0.2% aqueous emulsion of the following sterilizing agents: α-terpeniol and 3-carene respectively. The rate of consumption of the sterilizing agents is 1.2 kg/ha. The results of the tests are shown in Table 13 hereinbelow.

INDUSTRIAL APPLICABILITY

The method of the invention finds application in selection and seed production for raising and yielding of highly productive varieties and hybrids of crops.

We claim:

1. A method of sterilizing anthers of plants which comprises applying to said plants with a gametocidally effective amount of a sterilizing agent in combination with a diluent during the period of the fifth and/or sixth stage of organogenesis, said sterilizing agent being a terpenoid compound of the formula:

$$\begin{array}{c} CH_3 \\ \diagdown \\ C=C \\ \diagup \quad \diagdown \\ A \end{array} \begin{array}{c} H \\ \diagup \\ \end{array}$$

wherein $A = -CH-CH_2-CHCH_2-$
$\qquad\qquad\quad \diagdown\quad\diagup$
$\qquad\qquad\quad C(CH_3)_2$ , $-CH-CH_2-CHCH_2-$
$\quad\quad\quad\quad\quad\quad |$
$\quad\quad\quad\quad\quad\quad C(CH_3)=CH_2$ , $-CH_2-CH_2-CHCH_2-$
$\quad\quad\quad\quad\quad\quad\quad |$
$\quad\quad\quad\quad\quad\quad\quad C(CH_3)_2OCOCH_3$ , $-CH=CHC=CH-$
$\quad\quad\quad\quad\quad \diagdown$
$\quad\quad\quad\quad\quad HC(CH_3)_2$ ,

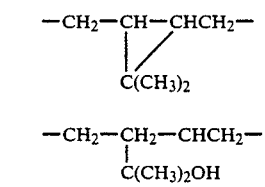

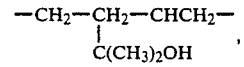

-continued $$-CH_2-CH_2-CCH_2- \\ \parallel \\ C(CH_3)_2 ,$$

or mixtures thereof.

2. A method as set forth in claim 1 in which said sterilizing agent is applied in the form of a 0.1–2.0% by weight water emulsion containing 0.1–0.5% by weight of emulsifier.

3. A method as set forth in claim 1 in which said plants are gramineous plants and sunflower.

4. A method according to claim 1 or 2 or 3 in which said sterilizing agent is applied repeatedly to said plant during the period of the fifth and/or sixth stage or organogenesis to assure a high level of sterilization of the anthers.

5. The method of claim 1, wherein A represents $$-CH-CH_2-CHCH_2- \\ \phantom{xx}| \diagup \\ \phantom{xxx}C(CH_3)_2$$

6. The method of claim 1, wherein A represents $$-CH-CH_2-CHCH_2- \\ \phantom{xx}| \\ \phantom{xxx}C(CH_3)=CH_2$$

7. The method of claim 1, wherein A represents $$-CH_2-CH_2-CHCH_2- \\ \phantom{xxxxx}| \\ \phantom{xxxxxx}C(CH_3)_2OCOCH_3$$

8. The method of claim 1, wherein A represents $$-CH=CHC=CH- \\ \phantom{xxxxx}\diagdown \\ \phantom{xxxxxx}HC(CH_3)_2$$

9. The method of claim 1, wherein A represents $$-CH_2-CH-CHCH_2- \\ \phantom{xxxx}| \diagup \\ \phantom{xxxxx}C(CH_3)_2$$

10. The method of claim 1, wherein A represents $$-CH_2-CH_2-CHCH_2- \\ \phantom{xxxxx}| \\ \phantom{xxxxxx}C(CH_3)_2OH$$

11. The method of claim 1, wherein A represents $$-CH_2-CH_2-CCH_2- \\ \phantom{xxxxx}\parallel \\ \phantom{xxxxxx}C(CH_3)_2$$

* * * * *